United States Patent [19]

Hörl

[11] Patent Number: 4,727,857
[45] Date of Patent: Mar. 1, 1988

[54] DEVICE FOR PRODUCING PULSATING MAGNETIC FIELDS FOR THERAPEUTIC PURPOSES

[75] Inventor: Alois Hörl, Munich, Fed. Rep. of Germany

[73] Assignee: Dieter Rau, Bad Ueberkingen, Fed. Rep. of Germany

[21] Appl. No.: 724,901

[22] Filed: Apr. 19, 1985

[30] Foreign Application Priority Data

Apr. 19, 1984 [DE] Fed. Rep. of Germany ....... 3414938

[51] Int. Cl.⁴ ............................................. A61B 17/52
[52] U.S. Cl. ........................................ 128/1.3; 128/790
[58] Field of Search .................. 128/1.3, 1.5, 362, 783, 128/790, 800

[56] References Cited

FOREIGN PATENT DOCUMENTS

| EP40053 | 11/1981 | European Pat. Off. ............. | 128/1.3 |
| 2510173 | 9/1976 | Fed. Rep. of Germany ....... | 128/1.3 |
| 3221544 | 12/1983 | Fed. Rep. of Germany ....... | 128/1.3 |

OTHER PUBLICATIONS

Mansfield et al, "NMR Imaging in Biomedicine", 4/13/82, pp. 297–310.

Primary Examiner—Edward M. Coven
Assistant Examiner—J. P. Lacyk
Attorney, Agent, or Firm—Sixbey, Friedman & Leedom

[57] ABSTRACT

A device for producing pulsating magnetic fields comprises a substrate rotatable about an axis and having disposed thereon at least one pair of magnets with a direction of magnetization substantially parallel to the rotational axis such that rotation of the substrate by 180° about its rotational axis transfers the pole faces of the magnets into each other and that there exists no symmetry of the pole faces relative to a plane which includes the rotational axis. The orientation of the pole faces of the magnets is such that during rotation of the substrate, magnetic forces are exerted radially with respect to the axis about which the substrate is rotated by drive structure provided for that purpose. In accordance with various embodiments, the magnets may be disposed upon one or both sides of the substrate and may be of rectangular, arcuate, wedge-like or other plate-like configurations.

19 Claims, 23 Drawing Figures

FIG. 19
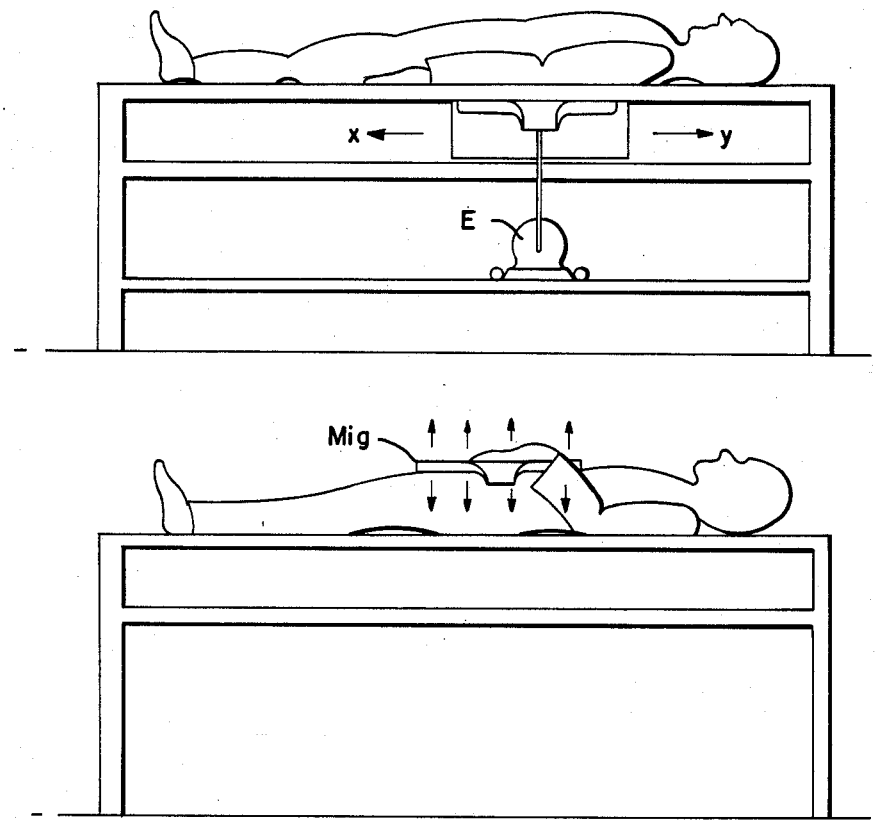
FIG. 20
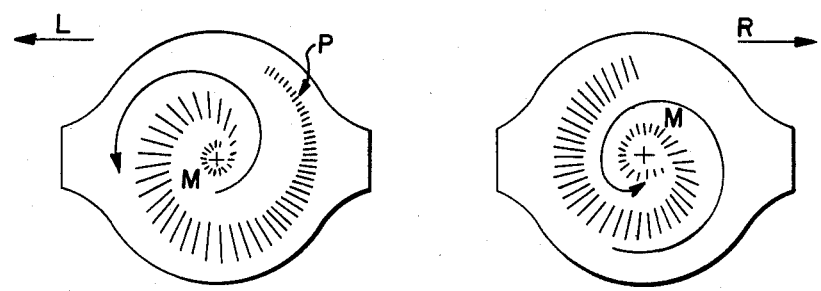
FIG. 8      FIG. 9

DEVICE FOR PRODUCING PULSATING MAGNETIC FIELDS FOR THERAPEUTIC PURPOSES

The invention is in the field of magnetotherapeutics and is particularly directed to a device for producing pulsating magnetic fields, in which magnetic fields are produced which rotate about a rotational axis.

From the French Patent Specification No. 324,317 and its Patent of Addition No. 1,703 a device has been known in which a U-shaped magnet is rotated about an axis extending in parallel to the legs of the U. This known configuration possesses radial symmetry, i.e., there is at least one plane which includes the rotational axis and in respect of which the pole faces are symmetrical. In that case the radial forces occurring above the plane of the pole faces due to a rotation of the magnet are completely independent of the direction of rotation of the magnet.

From the Austrian Patent Specification No. 354,621 it has been known to provide on a disc four groups of magnets with parallel polarisation relative to the rotational axis of the disc, each group of magnets practically occupying a 90°-sector of the disc and the directions of polarisation of adjacent groups being oppositely directed. This configuration also has radial symmetry and does not exhibit any dependence of the forces that are oriented away from and towards the rotational axis on the direction of rotation of the disc.

It is the object of the invention to provide a device for producing pulsating magnetic fields, which is capable of exerting radially inwardly or radially outwardly directed forces in dependence on the direction of rotation.

It is a further object of the invention to provide a device for producing pulsating magnetic fields, which exhibits a distinct dependence of the magnetic forces directed away from or towards the rotational axis on the direction of rotation.

It is a still further object of the invention to provide a device which produces fields in both directions of the rotational axis, both fields simultaneously having a centripetal force effect or simultaneously having a centrifugal force effect.

Below, embodiments of the invention with which these and further objects and advantages are achieved will be described with reference to the accompanying drawing, in which.

Figure 1:
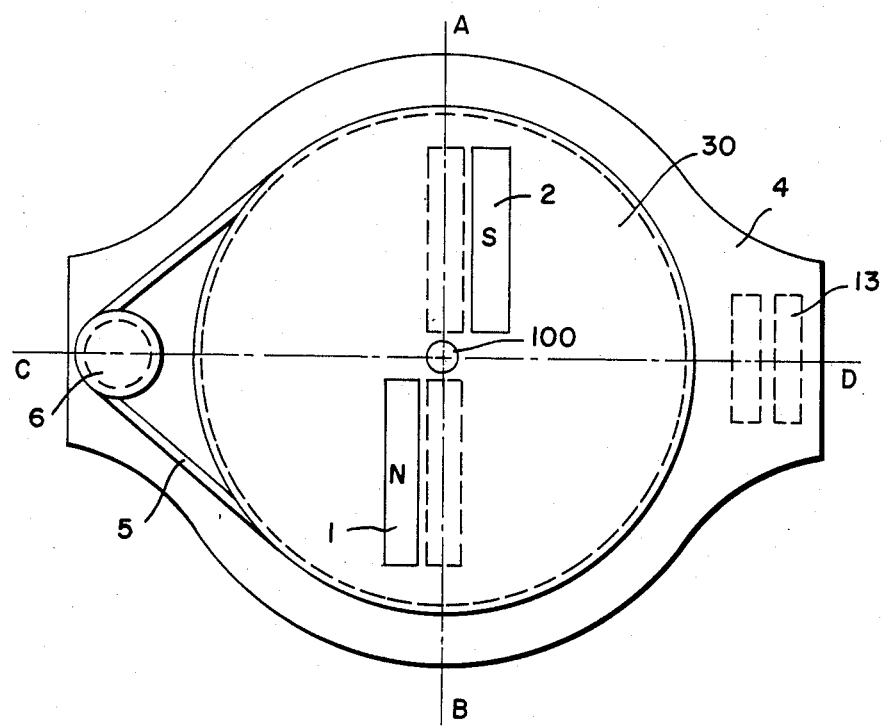
FIG. 1 is a schematic plan view of a first embodiment of the device.
Figure 2:
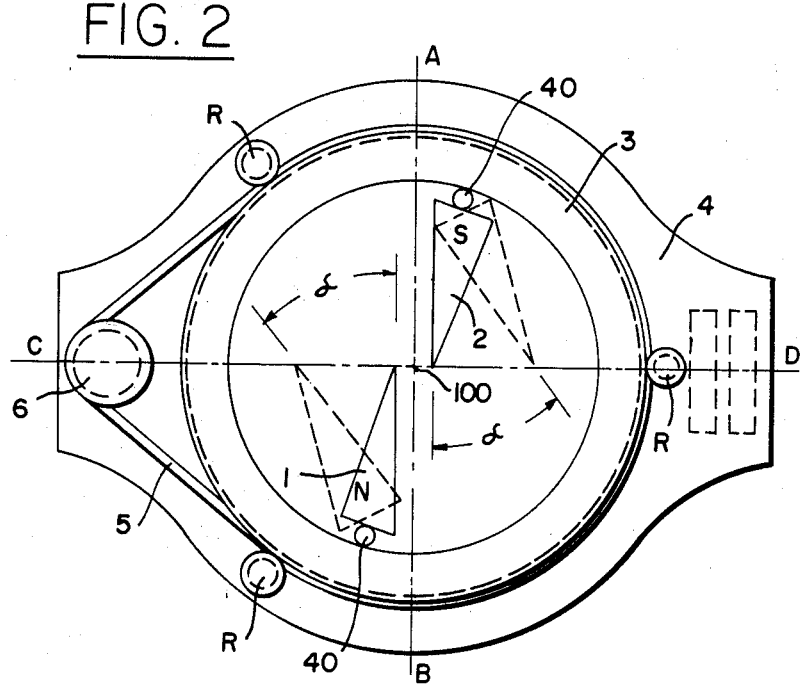
FIG. 2 is a plan view of a second embodiment of the device.
Figure 3:
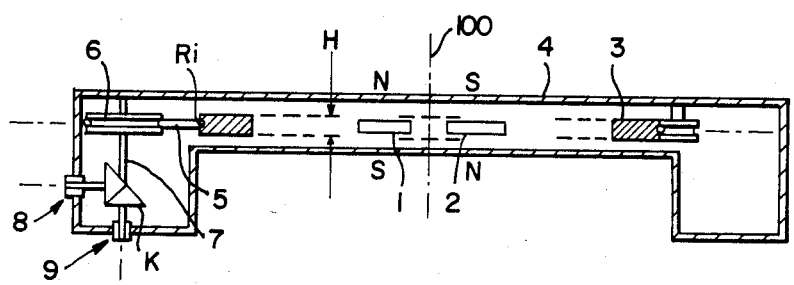
Figure 4:
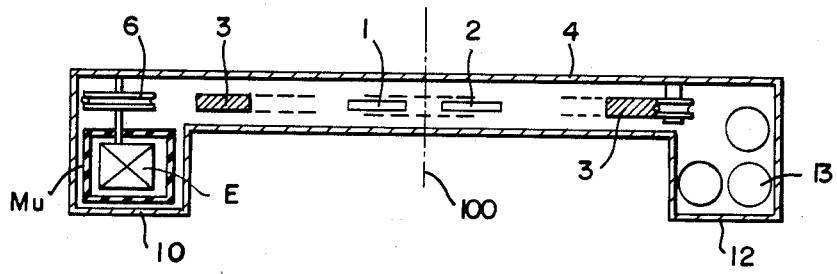
Figure 5:
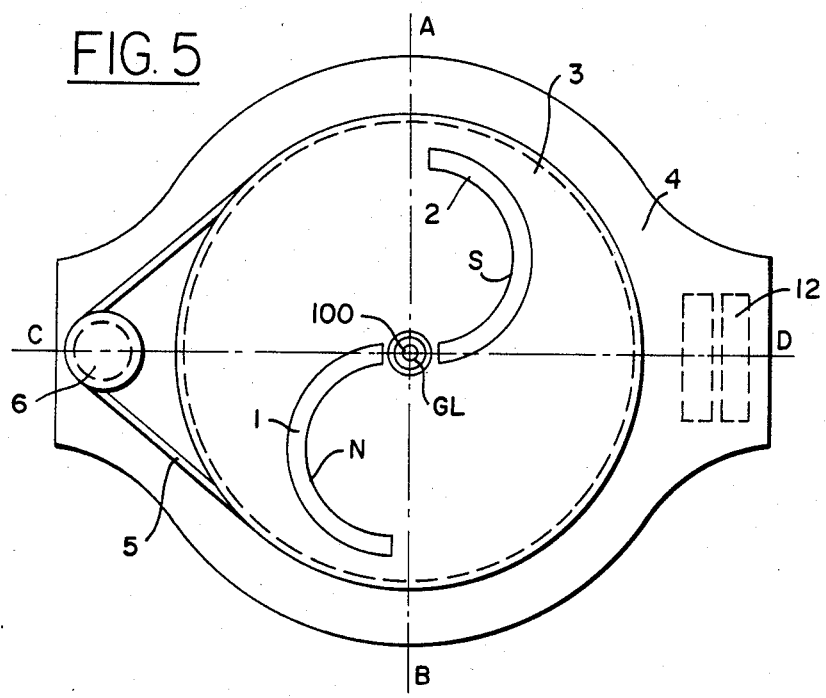
Figure 6:
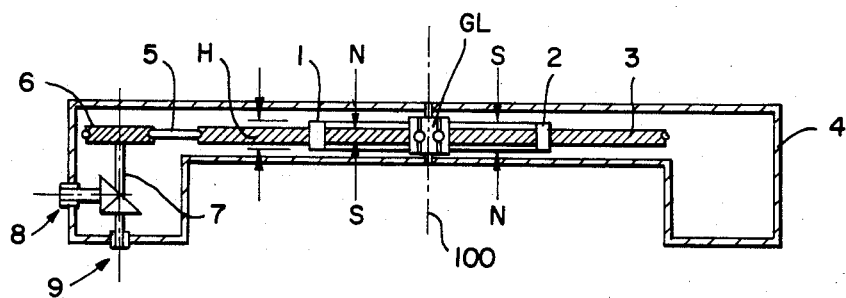
Figure 7:
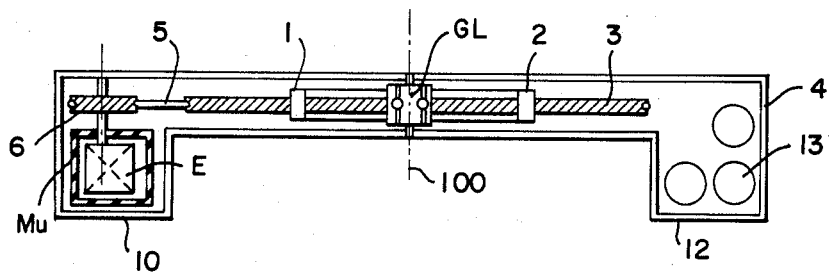
Figure 10:
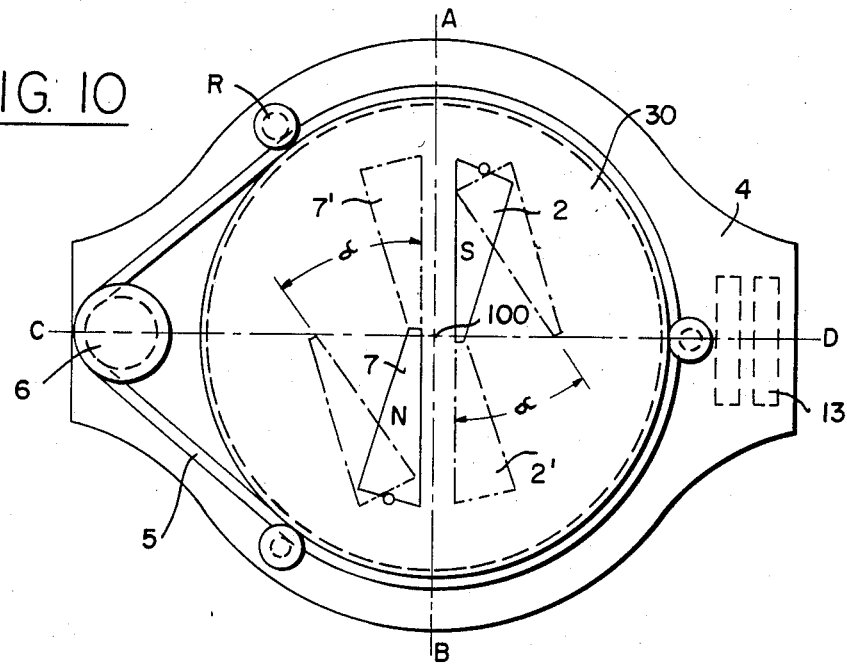
Figure 11:
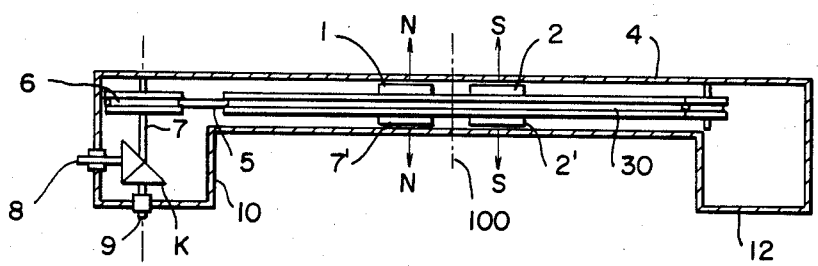
Figure 12:
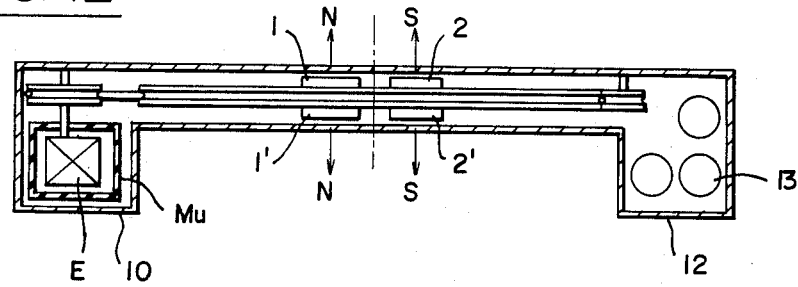
Figure 13:
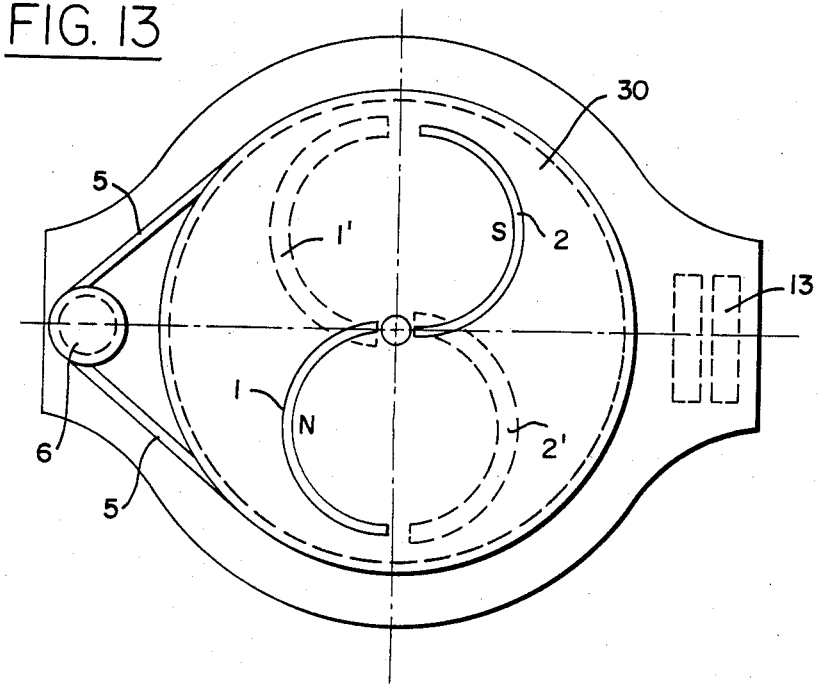
Figure 14:
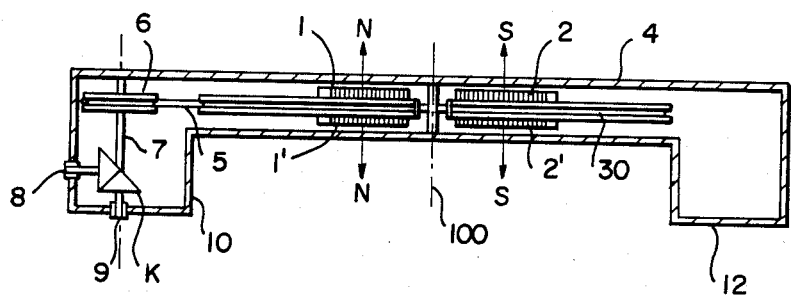
Figure 15:
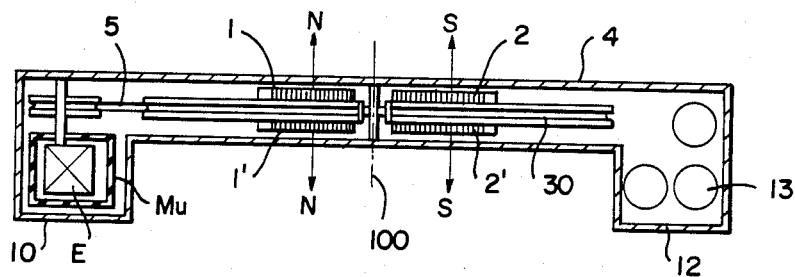
Figure 16:
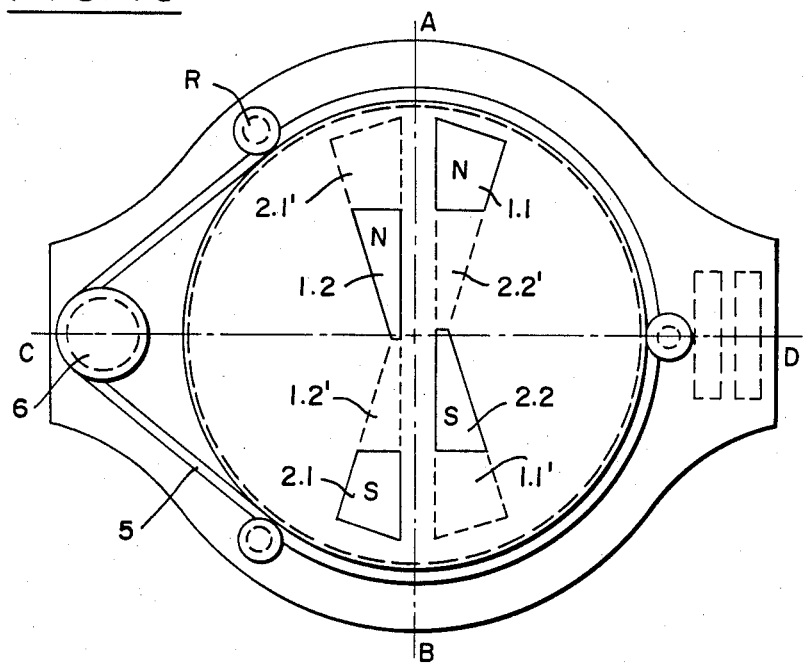
Figure 17:
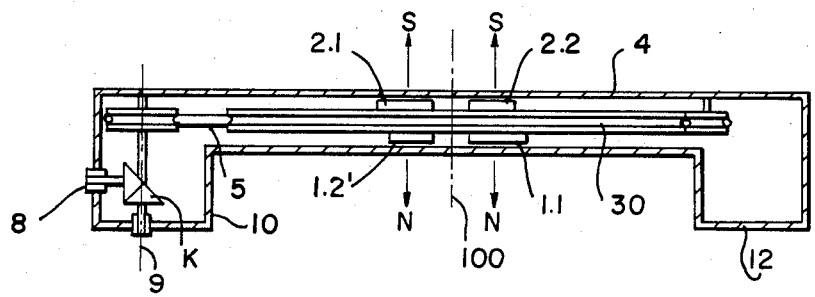
Figure 18:
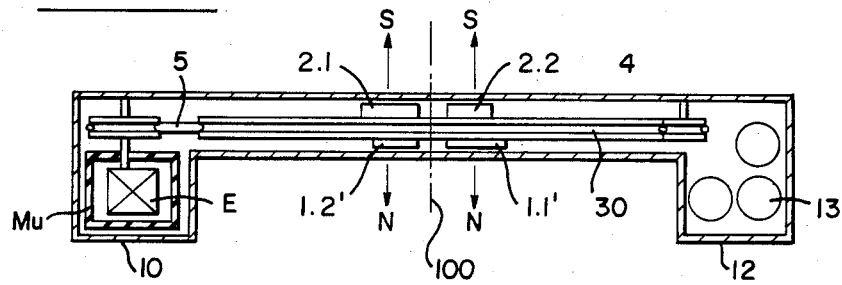
Figure 21:
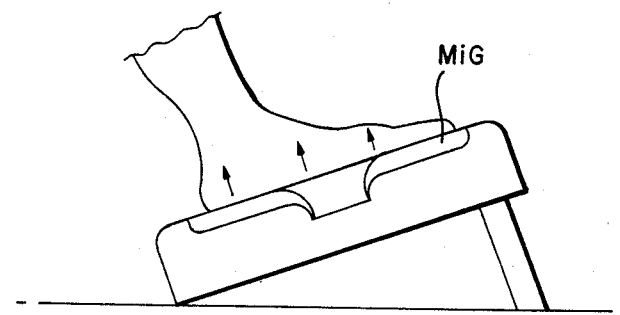
Figure 22:
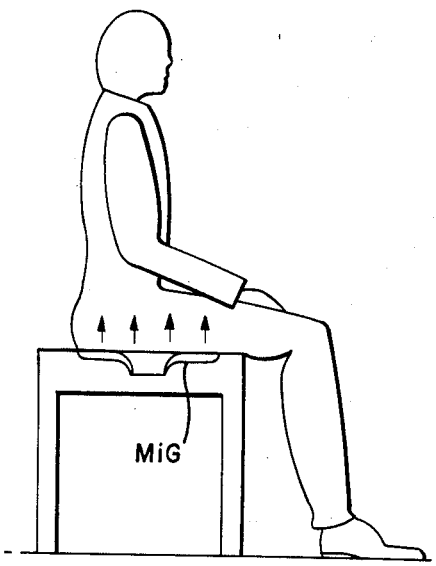

FIG. 3 and FIG. 4 are sectional views along the line C–D in FIG. 2 with different configurations of the drive means, FIG. 5 is a view similar to FIG. 2 illustrating a third embodiment of the device, FIG. 6 and FIG. 7 are sectional views along the line C–D of FIG. 5 with different configurations of the drive means, FIG. 8 and FIG. 9 are schematic views illustrating the way in which ferromagnetic granules is arranged on an antimagnetic disc above the magnetic device according to FIGS. 1 and 2 upon clockwise and anti-clockwise rotation of the magnet substrate, FIG. 10 is a view similar to FIG. 2 and illustrating a fourth embodiment of the invention, in which magnets are arranged identically on both sides of a substrate disc, FIG. 11 and FIG. 12 are sectional views along the line C–D of FIG. 10 with different configurations of the drive means, FIG. 13 is a view similar to FIG. 5 showing a fifth embodiment of the device, wherein magnets are identically arranged on both sides of a substrate disc, FIG. 14 and FIG. 15 are sectional views along the line C–D of FIG. 10 with different configurations of the drive means, FIG. 16 is a plan view of a sixth embodiment of the invention, wherein identically arranged magnets are provided on both sides of a substrate disc, FIG. 17 and FIG. 18 are sectional views along the line C–D of FIG. 16 with different configurations of the drive means, and FIG. 19 to FIG. 23 illustrate various examples for application.

As shown in FIG. 1, two permanent magnets 1, 2 are disposed on a disc 30 provided within a casing 4 and rotatable about an axis 100, said permanent magnets being offset by 180° around said rotational axis 100 and being polarised perpendicularly to the plane of the disc and parallel to the rotational axis 100 and in opposition to each other. The position of the two permanent magnets 1, 2 is obtained by offsetting each one from the dashed-line position by equal amounts in parallel to itself towards opposite sides of the plane A-B. Equivalently, the two magnets may be turned from the diametral position by equal angles about imaginary, radially outer axes in the same sense, i.e., both magnets may be turned either clockwise or anti-clockwise.

The height of the magnets as measured perpendicularly to the plane of the disc is small as compared to the length and width measured in the direction of the disc plane, i.e., as compared to the pole face dimensions. Therefore small magnetic plates are concerned. The length is selected such that each magnet extends substantially across the entire radius of the disc, whereas large free areas are provided between the magnets in circumferential direction of the disc. The preferred field intensity as measured on the pole faces of the permanent magnets preferably amounts to c.1000 gauss, and the distance from the object to be treated is preferably selected to be 10 mm. Preferably, the distance between the permanent magnets 1 and 2 disposed on the disc 30 and the object to be treated is determined by a plate of antimagnetic and electrically non-conductive material such as glass or plastics which is disposed above the disc, wherein the spacing between the plate and the magnet-carrying disc may be variable. In order to prevent distortions of the magnetic field, the disc 30 carrying the magnets and also the casing 4 are likewise selected to be of antimagnetic and electrically non-conductive material. Similarly, the shaft and the bearing for the rotatable disc 30 are also selected to be of antimagnetic material.

FIG. 2 illustrates a further embodiment of the device. The carrier for the magnets 1 and 2, which are of opposite polarity as in the embodiment of FIG. 1, is configured as an annular member 3. The permanent magnets, which again have a small height H in the direction of polarisation, i.e., in the direction of the rotational axis 100 (as will be apparent from FIGS. 3 and 4), are of wedge-like configuration and taper from the edge towards the centre of the annular member 3. The two permanent magnets 1 and 2 are disposed at a 180° offset relative to the rotational axis in an arrangement which is obtained when both wedge-like magnets 1 and 2 are pivoted anti-clockwise from a diametral orientation by equal angles about an axis disposed in the vicinity of their outer edges. Moreover, in the embodiment illustrated in FIG. 2 the pivoted position of the magnets 1 and 2 is variable, the magnets being adapted to be pivoted anti-clockwise from the fullline position about an additional angle α right to the dashed-line position. The pivot points are indicated at 40 and are disposed on the inner periphery of the annular member 3. In any event the symmetry is such that rotation of the annular member about 180° about its rotational axis will transfer both magnets into each other.

As will be particularly apparent from FIGS. 3 and 4, the magnets and the annular member are provided in a completely closed casing of antimagnetic and electrically non-conductive material. The flat cover surface of the casing 4, on which the object to be treated will rest, at the same time determines the spacing of said object relative to the magnets. This spacing preferably may be 5 to 10 mm.

The annular member 3 is driven through a belt 5 trained about the periphery of the annular member 3 and a driving roller 6 coaxial therewith. Furthermore, the periphery of the annular member 3 is provided with three rollers R having annular grooves formed therein for axially locating the annular member 3 and the driving belt 5. The driving roller 6 is driven by a shaft 7 extending in parallel to the axis of the annular member, the shaft 7 in its turn being adapted to be driven by a shaft 9 disposed as an extension thereof, or by a shaft 8 extending perpendicularly thereto and with a bevel gear interposed therebetween; either one or the other of the shafts 8 and 9 may selectively be coupled to an electric motor. The electric motor is disposed externally of the casing 4, so that any disturbance of the field caused thereby may be avoided.

The modification illustrated in FIG. 4 includes a mumetal-shielded (Mu) electric motor E peripherally disposed within a handle segment 10 of the casing, while accumulators 13 for the supply of power thereto are disposed in a diametrally opposite handle segment 12.

The wedge-like configuration of the two permanent magnets 1 and 2 causes a magnetic field within the swept circular area which, when the magnets rotate about the axis 100, is relatively independent with respect to time from the distance to the rotational axis. The extra-radial arrangement of the magnets causes an unsymmetry of the magnetic forces in dependence on the sense of rotation of the annular member 3 with the permanent magnets 1 and 2 provided thereon, which unsymmetry must be taken into account therapeutically.

This unsymmetry of the magnetic forces is illustrated in FIGS. 8 and 9. Upon anti-clockwise rotation—when viewed in accordance with FIG. 2—ferromagnetic granules disposed on the casing will spread helically from the centre towards the periphery, whereas upon clockwise rotation the granules will spread helically from the periphery towards the centre. This effect shows a dependence on the pivot angle of the two permanent magnets 1 and 2.

An almost radial centripetal or centrifugal pattern of such granules is apparent in the embodiment illustrated in FIG. 5, in which the permanent magnets, while still being polarised opposite to each other and parallel to the rotational axis, are not wedge-shaped but are both arcuate with the curvature lying in the plane of rotation. Again, the two magnets are offset by 180° relative to the rotational axis so that together they form an S-configuration.

In the embodiment illustrated in FIG. 5, the two magnets 1 and 2 are not provided on the inside of an annular member 3 but are inserted into a disc 30 which is supported on an antimagnetic bearing GL.

The insertion of the two magnets 1, 2 into the disc 30, which may also be provided in a modification of the embodiment shown in FIG. 1, or the provision of the two magnets on the inside of the annular member 3 is performed such that symmetrical relationships result for the position of the magnets relative to the plane of the disc or annular member. In conjunction with the chosen configuration of the casing in such a way that casing portions above and beneath the disc or annular member are likewise symmetrically positioned relative to the plane of the disc or annular member, the devices may be used towards either side at equal field intensity conditions on the site of application. Turning-over of the device will then reverse the field dynamics (centrifugal-centripetal) at the site of application without a reversal of the direction of rotation of the motor.

Possible drive means for driving the disc will be apparent from FIGS. 6 and 7 and correspond to the drive means shown in FIG. 3.

The FIGS. 10 and 11 as well as 10 and 12, respectively, show a dual-side embodiment derived from the embodiment illustrated in FIGS. 2 and 3 as well as 2 and 4, respectively, in which the magnets 1, 2 and 1', 2' are disposed on both sides of a disc 30. In this case the disc 30 is made of a magnetic material so as to shield the fields of the magnets 1, 2 and 1', 2' disposed on either side of the disc relative to each other. The arrangement of the magnets 1, 2 and 1', 2' on either side of the disc 30 is selected such that, when viewing one side of the disc 30, the magnets provided on said side have the same relative arrangement as will appear for the magnets on the other side of the disc when viewing said other side. Relative angular offset of the two arrangements is permissible. In other words, by turning the disc 30 about the axis C-D of FIG. 10 (and optionally by a rotation about the rotational axis 100) the magnets provided on one side of the disc are transferred into the magnets 1', 2' provided on the other side of the disc.

Figure 23:
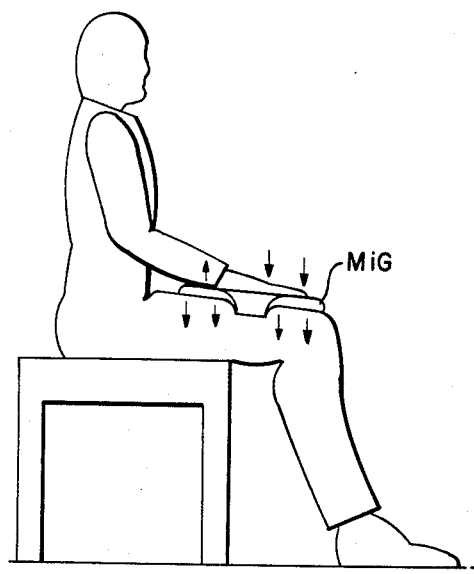

Upon application of the device from both sides, such as shown, for example, in FIG. 23 where the patient holds the device on his thighs and rests his hands on the device, it is possible with such an arrangement of the magnets 1, 2 and 1', 2' that the same field dynamics are achieved on either side, i.e., with a centrifugal or with a centripetal effect on both sides in accordance with the direction of rotation of the disc.

As shown in FIG. 10, the magnets 1, 2 and 1', 2' may be pivoted in a plane parallel to the plane of the disc 30 (the ability to pivot is shown in dashed lines only for the magnets 1, 2 on the one side).

The FIGS. 13 and 14 or 13 and 15, respectively, show an embodiment which has the same relationship in respect of the arrangement of the magnets disposed on both sides of the magnetically shielding disc 30 to the embodiment of FIGS. 5 and 6 or 5 and 7, respectively, as has the embodiment of FIGS. 10 and 11 or 10 and 12, respectively, to that of FIGS. 2 and 3 or 2 and 4, respectively.

Here, too, the result is that in both directions of application the same either inwardly acting or outwardly acting field dynamics are respectively achieved.

Although not illustrated in detail, the embodiment shown in FIG. 1 may also be modified such that magnets with the same relative arrangement are provided on both sides of a magnetically shielding disc.

The embodiment illustrated in FIGS. 16 and 17 or 16 and 18, respectively, provides on both sides of the magnetically shielding disc 30 split wedge-like magnets, viz., 1.1 and 1.2 as well as 2.1 and 2.2 on the one side and 1.1' and 1.2' as well as 2.1' and 2.2' on the other side, wherein the parts having the same direction of polarisation are respectively offset towards opposite sides relative to the diametral position defined in FIG. 16 by the axis A-B, and the radially inner parts are offset towards sides of A-B which are opposite to the sides towards which the radially outer parts are offset.

In accordance with the explanations given in respect of the magnet arrangements of FIGS. 10 and 13, the magnet arrangement on the other side of the disc 30 is selected such that the magnets on the one side may be transferred into the magnets of the other side by an imaginary turning of the disc (and possibly a rotation about the rotational axis 100).

Instead of the wedge-like magnets illustrated in FIG. 16 it is also possible to use constant-width magnets, i.e., rectangular magnets.

With an embodiment as shown in FIG. 16, centrifugal and centripetal force effects are simultaneously obtained.

A device may have split magnets on one side thereof and unitary magnets on the other side thereof.

In all of the illustrated embodiments, separate magnets have been shown for forming the pole faces in the desired arrangement. Basically, however, it is also possible to form unlike pole faces as the two ends of a single magnet which extends behind the plane in which these pole faces are disposed.

The FIGS. 19 to 23 show examples for application of the device for producing pulsating magnetic fields. In all cases provision has been made for the disc plane to lie either horizontally or at least almost horizontally. The therapeutically favorable rotational frequency of the magnetic field is in the order of 1 Hz. The lateral disposition of the motor permits application on both sides as shown in FIGS. 20 and 23. For the application shown in FIG. 19, the entire device may be moved beneath a couch on which the patient rests.

Clinical tests have confirmed the therapeutic effects as follows:

A rotational direction of the device with a centripetal force effect (rotation in offset direction, i.e. clockwise in the illustrated embodiments) has a relaxing, sedative effect, while the reverse rotational direction has a tonicising effect.

For rotation with centripetal force effect the following results have been obtained:
1. A marked improvement of circulatory disturbances appeared in most cases after only a few minutes, this effect sometimes appearing after as much as 15 to 20 minutes, depending on the overall state of the test person.
2. Conditions of muscular tension were rapidly decreased. This was verified in a statistically significant way by examining the leg muscles with the aid of superficial myography.

What is claimed is:

1. A device for producing pulsating magnetic fields for therapeutic purposes in which, on a substrate rotatable about an axis, at least one pair of magnets is disposed in such a way that first pole faces of opposite polarity, which face in one direction of the rotational axis and have a direction of magnetisation substantially parallel to the rotational axis at a surface thereof, are provided in such configuration and position that rotation of the substrate by 180 degrees about the rotational axis will substantially transfer the magnetic fields produced by the first pole faces into each other with a reversal of the field direction, wherein the first pole faces occupy only a minor portion of the angular range swept by them upon rotation of the substrate about the rotational axis and are arranged and shaped such that the field produced thereby at any time has no radial symmetry, i.e., has no plane including the rotational axis as the plane of symmetry.

2. A device as claimed in claim 1, wherein the first pole faces are of elongated configuration and extend with their longitudinal extension from a region of greater distance from the rotational axis into a region of lesser distance from the rotational axis.

3. A device as claimed in claim 2, wherein the first pole faces have rectangular cross-section.

4. A device as claimed in claim 2, wherein the cross-section of the first pole faces becomes narrower with decreasing distance from the rotational axis.

5. A device as claimed in claim 3, wherein the non-radially-symmetrical arrangement is obtained in that the first pole faces are offset with their longitudinal axis towards opposite sides of a plane including the rotational axis.

6. A device as claimed in claim 4, wherein the first pole faces are arranged with their longitudinal axes pivoted towards opposite sides of a plane including the rotational axis, and the pivot angle is variable.

7. A device as claimed in claim 2, wherein the first pole faces are arcuate and in combination define an S-configuration.

8. A device as claimed in claim 2, wherein further first pole faces of opposite polarity are provided at a different radial distance from the rotational axis than said first pole faces of opposite polarity, and wherein said first and said further first pole faces are disposed in relatively opposite directions outside of the radial symmetry.

9. A device as claimed in claim 7, wherein second pole faces facing into the other direction of the rotational axis are provided, which relative to each other are disposed at the same radial unsymmetry as the first pole faces, and wherein magnetic shielding means is provided between said first and said second pole faces.

10. A device as claimed in claim 8, wherein second and further second pole faces facing into the other direction of the rotational axis are provided, which relative to each other are arranged at the same radial unsymmetry as said first and said further first pole faces, and wherein magnetic shielding means is provided between said first and said further first pole faces, on the one hand, and said second and said further second pole faces, on the other hand.

11. A device as claimed in claim 8, wherein second pole faces facing in the other direction of the rotational axis are provided which relative to each other are arranged at the same radial unsymmetry as said first pole faces, and wherein magnetic shielding means is provided between said first and said further first pole faces, on the one hand, and said second pole faces, on the other hand.

12. A device as claimed in claim 1, wherein second pole faces facing into the other direction of the rotational axis are provided, which relative to each other are disposed at the same radial unsymmetry as the first pole faces, and wherein magnetic shielding means is provided between said first and second pole faces.

13. A device as claimed in claim 2, wherein second pole faces facing into the other direction of the rotational axis are provided, which relative to each other are disposed at the same radial unsymmetry as the first pole faces, and wherein magnetic shielding means is provided between said first and said second pole faces.

14. A device as claimed in claim 3, wherein second pole faces facing into the other direction of the rotational axis are provided, which relative to each other are disposed at the same radial unsymmetry as the first pole faces, and wherein magnetic shielding means is provided between said first and second pole faces.

15. A device as claimed in claim 4, wherein second pole faces facing into the other direction of the rotational axis are provided, which relative to each other are disposed at the same radial unsymmetry as the first pole faces, and wherein magnetic shielding means is provided between said first and second pole faces.

16. A device as claimed in claim 5, wherein second pole faces facing into the other direction of the rotational axis are provided, which relative to each other are disposed at the same radial unsymmetry as the first pole faces, and wherein magnetic shielding means is provided between said first and second pole faces.

17. A device as claimed in claim 6, wherein second pole faces facing into the other direction of the rotational axis are provided, which relative to each other are disposed at the same radial unsymmetry as the first pole faces, and wherein magnetic shielding means is provided between said first and second pole faces.

18. A device for producing pulsating magnetic fields for therapeutic purposes comprising a carrier mounted for rotation about an axis, means for rotating the carrier about said axis, and at least one pair of magnets, wherein said magnets are disposed in a manner forming a means for exerting, upon rotation of said carrier about said axis, magnetic forces that are directed radially with respect to said axis and that produce a magnetic field which is at all times free of radial symmetry with respect to said axis, and wherein the magnets are positioned relative to each other in a manner such that, upon rotation of the carrier by 180 degrees about said axis, faces of said pair of magnets which are of opposite polarity and face in a common direction parallel to said axis will have exchanged placed.

19. A device according to claim 18, further comprising a casing fully enclosing said carrier and said pair of magnets.

* * * * *